United States Patent
Lee et al.

(10) Patent No.: US 12,198,089 B2
(45) Date of Patent: Jan. 14, 2025

(54) DRIVER EVALUATION MANAGEMENT METHOD AND CONTROL SERVER USING THE SAME

(71) Applicants: Hyundai Motor Company, Seoul (KR); Kia Corporation, Seoul (KR)

(72) Inventors: Hanul Lee, Incheon (KR); Sojeong Kim, Seoul (KR)

(73) Assignees: HYUNDAI MOTOR COMPANY, Seoul (KR); KIA CORPORATION, Seoul (KR)

( * ) Notice: Subject to any disclaimer, the term of this patent is extended or adjusted under 35 U.S.C. 154(b) by 162 days.

(21) Appl. No.: 17/734,565

(22) Filed: May 2, 2022

(65) Prior Publication Data

US 2023/0186220 A1    Jun. 15, 2023

(30) Foreign Application Priority Data

Dec. 13, 2021  (KR) ......................... 10-2021-0178082

(51) Int. Cl.
*G06Q 10/0639* (2023.01)
*G01N 33/00* (2006.01)
(Continued)

(52) U.S. Cl.
CPC ..... *G06Q 10/0639* (2013.01); *G01N 33/0004* (2013.01); *G06Q 30/0282* (2013.01); *G06Q 50/40* (2024.01)

(58) Field of Classification Search
None
See application file for complete search history.

(56) References Cited

U.S. PATENT DOCUMENTS 10,697,784 B1 * 6/2020 Li ........................... H04L 67/00
2006/0276960 A1 * 12/2006 Adamczyk ............ G06Q 10/06
701/516
(Continued)

FOREIGN PATENT DOCUMENTS

| KR | 101491368 B1 | 2/2015 |
| KR | 102027753 B1 | 11/2019 |
| KR | 102272500 B1 | 7/2021 |

OTHER PUBLICATIONS

Goh CC, Kamarudin LM, Zakaria A, Nishizaki H, Ramli N, Mao X, Syed Zakaria SMM, Kanagaraj E, Abdull Sukor AS, Elham MF. Real-Time In-Vehicle Air Quality Monitoring System Using Machine Learning Prediction Algorithm. Sensors (Basel). Jul. 1, 2021 ( Year: 2021).*

(Continued)

*Primary Examiner* — Stephanie Z Delich
(74) *Attorney, Agent, or Firm* — SLATER MATSIL, LLP

(57) ABSTRACT

An embodiment driver evaluation method performed by a control server includes receiving air quality data from a sensor in a vehicle, determining an internal state of a vehicle as a smoking state, an air pollution state, or a normal state based on the air quality data, transmitting a driving grade range to a passenger terminal, the driving grade range having an adjusted evaluation score reduced by at least one level from a reference score as a highest point in response to the determined internal state being the smoking state, determining a driver evaluation score for driving of the vehicle based on a driving grade in response to the driving grade within the driving grade range being received from the passenger terminal, and storing the driver evaluation score in a database.

11 Claims, 3 Drawing Sheets

(51) Int. Cl.
 G06Q 30/0282 (2023.01)
 G06Q 50/40 (2024.01)

(56) References Cited

U.S. PATENT DOCUMENTS

| | | | |
|---|---|---|---|
| 2013/0066688 A1* | 3/2013 | Pinkus | G06Q 10/0639 |
| | | | 705/7.41 |
| 2014/0309849 A1* | 10/2014 | Ricci | H04W 4/60 |
| | | | 701/33.4 |
| 2016/0210851 A1* | 7/2016 | Oshima | G08G 1/0133 |
| 2020/0111189 A1* | 4/2020 | Yeung | G06Q 50/30 |
| 2020/0175783 A1* | 6/2020 | Adams | G07C 5/0808 |
| 2020/0286310 A1* | 9/2020 | Carver | G07C 5/02 |

OTHER PUBLICATIONS

Goh CC, Kamarudin LM, Zakaria A, Nishizaki H, Ramli N, Mao X, Syed Zakaria SMM, Kanagaraj E, Abdull Sukor AS, Elham MF. Real-Time In-Vehicle Air Quality Monitoring System Using Machine Learning Prediction Algorithm. Sensors (Basel). Jul. 2, 20211 ( (Year: 2021).*

* cited by examiner

DRIVER EVALUATION MANAGEMENT METHOD AND CONTROL SERVER USING THE SAME

CROSS-REFERENCE TO RELATED APPLICATIONS

This application claims the benefit of Korean Patent Application No. 10-2021-0178082, filed on Dec. 13, 2021, which application is hereby incorporated herein by reference.

TECHNICAL FIELD

The present disclosure relates to a driver evaluation management method and a control server using the same.

BACKGROUND

Recently, various problems due to fine dust, ultra-fine dust, yellow dust, etc. have occurred, and various methods for improving indoor air quality are being discussed. The air inside a vehicle may also be polluted with fine dust, etc., and if the air inside the vehicle belonging to a corporation, such as a taxi, is contaminated, there is a possibility that service satisfaction of passengers in the vehicle may deteriorate.

In addition, although smoking in taxi vehicles is prohibited by law, there are cases where drivers smoke in the vehicles. A passenger aboard this vehicle will inhale an unpleasant odor caused by the driver's smoking, as well as inhaling the polluted air. As such, due to the driver's smoking in the vehicle, satisfaction with the service of the passengers may deteriorate.

Therefore, there is a need for a method that can improve the internal environment of vehicles belonging to corporations such as in taxis.

The above information disclosed in this Background section is only for enhancement of understanding of the background of the invention, and therefore it may contain information that does not form the prior art that is already known to a person of ordinary skill in the art.

SUMMARY

The present disclosure is intended to provide a method and a control server using the method to evaluate a driver of a corporate vehicle such as a taxi based on the internal environment of the vehicle.

According to one embodiment of the present invention, a driver evaluation method of a vehicle including a sensor unit includes receiving, by a control server, air quality data from the sensor unit, determining, by the control server, the internal state of the vehicle as one of a smoking state, an air pollution state, and a normal state based on the air quality data, transmitting, by the control server, a driving grade range having an adjusted evaluation score reduced by at least one level from a reference score as a highest point to a passenger terminal if the determined internal state is the smoking state, determining, by the control server, a driver evaluation score for the driving of the vehicle based on the driving grade if a driving grade within the driving grade range is received from the passenger terminal, and storing, by the control server, the driver evaluation score in a database.

The driver evaluation method may further include determining, by the control server, an adjusted score to which a penalty is applied as the driver evaluation score for the driving of the vehicle if the driving grade is not received from the passenger terminal.

The driver evaluation method may further include transmitting, by the control server, a signal indicating air pollution notification to the driver terminal and the passenger terminal if the determined internal state is the air pollution state, receiving, by the control server, first air quality data from the sensor unit after a predetermined time has elapsed from the time when the signal indicating the air pollution notification is transmitted, and determining, by the control server, whether to determine the vehicle internal state as the normal state based on the first air quality data.

The driver evaluation method may further include determining, by the control server, the driver evaluation score for the driving of the vehicle based on the driving grade if the vehicle internal state is not determined as the normal state by the first air quality data and the driving grade is not received from the passenger terminal.

The driver evaluation method may further include determining, by the control server, the adjusted score to which a penalty is applied as the driver evaluation score for the driving of the vehicle if the vehicle internal state is not determined as the normal state based on the first air quality data and the driving grade is not received from the passenger terminal.

The driver evaluation method may further include transmitting, by the control server, a signal that the air pollution notification is finished to the driver terminal and the passenger terminal if the vehicle internal state is determined as the normal state based on the first air quality data.

The driver evaluation method may further include determining, by the control server, the vehicle internal state as the normal state if the determined internal state is not the smoking state or the air pollution state.

The driver evaluation method may further include forwarding, by the control server, a call request for the vehicle to one of a plurality of driver terminals based on the driver evaluation score.

A driver evaluation management system according to another embodiment of the present invention includes a sensor unit included in a vehicle and measuring a concentration of a smoking index capable of being determined as a smoking state and a pollution index capable of being determined as a pollution state in air to generate air quality data and a control server determining a vehicle internal state as one of a smoking state, an air pollution state, and a normal state based on the air quality data if the air quality data is received from the sensor unit, providing a notification to a driver terminal and a passenger terminal if the vehicle internal state is determined as the smoking state or the air pollution state, and determining the driver evaluation score based on the vehicle internal state.

The control server may include a communication unit that is connected to the sensor unit, the driver terminal, and the passenger terminal via a wireless network, receives the air quality data from the sensor unit, and transmits a signal indicating smoking notification or a signal indicating air pollution notification to the driver terminal and the passenger terminal, a controller that determines the vehicle internal state as one of the smoking state, the air pollution state, and the normal state from the air quality data, determines a driver evaluation score based on the driving grade received from the passenger terminal according to the vehicle internal state, or determines the adjusted score to which a penalty is applied as the driver evaluation score according to the determined vehicle internal state, and a storage unit storing the driver evaluation score in a database.

If the controller determines the vehicle internal state as the smoking state, the communication unit may request input of the driving grade to the passenger terminal after the driving of the vehicle is finished and transmit the adjusted evaluation score of which the highest point of the driving grade range is reduced by at least one level from the reference evaluation score.

If a signal indicating the driving grade is received from the passenger terminal, the controller may determine the driver evaluation score based on the received driving grade.

If a signal indicating the driving grade is not received from the passenger terminal, the controller may determine the adjusted score to which the penalty is applied as the driver evaluation score.

If the controller determines the vehicle internal state as the air pollution state, the communication unit may transmit a signal indicating the air pollution notification to the driver terminal and the passenger terminal, and receive first air quality data from the sensor unit after a certain time has elapsed from a time point at which a signal indicating the air pollution notification is transmitted.

If the controller does not determine the vehicle internal state as the normal state based on the first air quality data, the communication unit may request input of driving grade to the passenger terminal after the end of the driving for the vehicle, and transmit an adjusted evaluation score of which a highest point of the driving grade range is reduced by at least one level from the reference evaluation score.

If a signal representing the driving grade is received from the passenger terminal, the controller may determine the driver evaluation score based on the received driving grade.

If a signal indicating the driving grade is not received from the passenger terminal, the controller may determine the adjusted score to which the penalty is applied as the driver evaluation score.

The control server may forward a call request for the vehicle to one of a plurality of driver terminals based on the determined driver evaluation score.

In providing the driver evaluation service, by measuring the air quality in the vehicle so that the measured result may be reflected in the driver evaluation, the driver evaluation management method and the control server using the same that may improve the satisfaction of consumers who receive the vehicle use service to which the driver evaluation service is applied, and may efficiently manage a plurality of drivers, may be provided.

Figure 1:
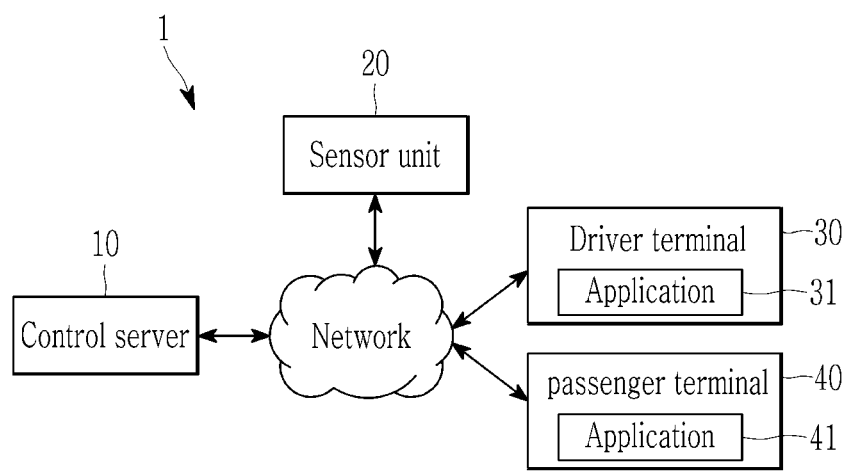
FIG. 1 is a block diagram schematically showing a configuration of a driver evaluation management system according to an exemplary embodiment.

The following reference identifiers may be used in connection with the accompanying drawings to describe exemplary embodiments of the present disclosure.

1: driver evaluation management system
10: control server
110: controller
120: communication unit
130: storage unit
20: sensor unit
30: driver terminal
31: application
40: passenger terminal
41: application

DETAILED DESCRIPTION OF ILLUSTRATIVE EMBODIMENTS

Hereinafter, embodiments disclosed in the present specification will be described in detail with reference to the accompanying drawings. In the present specification, the same or similar components will be denoted by the same or similar reference numerals, and an overlapped description thereof will be omitted. The terms "module" and "unit" for components used in the following description are used only in order to easily make a specification. Therefore, these terms do not have meanings or roles that distinguish them from each other in themselves. Further, in describing embodiments of the present specification, when it is determined that a detailed description of the well-known art associated with the present invention may obscure the gist of the present invention, it will be omitted. In addition, the accompanying drawings are provided only in order to allow embodiments disclosed in the present specification to be easily understood and are not to be interpreted as limiting the spirit disclosed in the present specification, and it is to be understood that the present invention includes all modifications, equivalents, and substitutions without departing from the scope and spirit of the present invention.

Terms including ordinal numbers such as first, second, and the like will be used only to describe various components, and are not interpreted as limiting these components. The terms are only used to differentiate one component from other components.

In the specification, the word "comprise" or "has" is used to specify existence of a feature, a number, a process, an operation, a constituent element, a part, or a combination thereof, and it will be understood that existence or additional possibility of one or more other features or numbers, processes, operations, constituent elements, parts, or combinations thereof are not excluded.

In a configuration for controlling other configurations in a specific control condition among configurations according to an embodiment, a program implemented as a set of instructions embodying a control algorithm necessary to control other configurations may be installed. The control configuration may generate output data by processing input data and stored data according to the installed program. The control configuration may include a non-volatile memory to store the programs and a memory to store the data.

FIG. 1 is a block diagram schematically showing a configuration of a driver evaluation management system according to an exemplary embodiment.

The driver evaluation management system 1 may include a control server 10, a sensor unit 20, a driver terminal 30, and a passenger terminal 40. An information transmission/reception between the control server 10, the sensor unit 20, the driver terminal 30, and the passenger terminal 40 may be implemented by various communication methods through a wired/wireless network. A service to which the driver evaluation management system 1 according to an exemplary embodiment is applied to a driver of a vehicle such as a taxi is hereinafter referred to as a vehicle use service. The vehicle may be a taxi.

In FIG. 1, the number of the passenger terminals is shown as one, but the invention is not limited thereto, and the driver evaluation management system 1 may include at least one passenger terminal.

The control server 10 may determine the vehicle internal state from the air quality data received from the sensor unit 20 as one of the smoking state, the air pollution state, and the normal state, and when the vehicle internal state is determined to be the smoking state or the air pollution state, may provide information to the driver terminal 30 and the passenger terminal 40, and may determine a driver evaluation score based on the vehicle internal state. The control server 10, when the vehicle internal state is not the smoking state or the air pollution state, may determine the vehicle internal state as the normal state. The driver evaluation score may be a score evaluated for the driving for the driver using the driver terminal 30 who operated the vehicle.

The air quality data, as data capable of determining air quality, may include a smoking index that may be determined as the smoking state and a pollution index that may be determined as the air pollution state. The smoking index may include a total volatile organic compound (TVOC) level, and the pollution index may include a PM 2.5 level and a PM 10 level. PM 2.5 is a concentration of particles with a diameter of 2.5 micrometers or less in air, and may represent the concentration of ultrafine dust in air. PM 10 is a concentration of particles with a diameter of 10 micrometers or less in air, and may represent the concentration of fine dust in air.

The sensor unit 20 may generate the air quality data by measuring the concentration of the smoking index and the pollution index in air. The sensor unit 20 may include an air quality sensor (AQS) and an electronic nose. The electronic nose may refer to a technology that can measure volatile organic compounds based on the characteristics of odor molecules and materials. The sensor unit 20 may be installed inside the vehicle.

The driver who wants to operate the vehicle may install an application 31 in the driver terminal 30 to receive the vehicle use service. The driver terminal 30 may be a terminal positioned inside the vehicle. For example, the driver terminal 30 may be implemented in a form of an In-Vehicle Infotainment (IVI) system positioned in the first row of the vehicle. Hereinafter, the transmission and reception of the signal by the control server 10 with the driver terminal 30 through the application 31 may be represented as transmission and reception of a signal to and from the driver terminal 30.

The passenger may install an application 41 on a passenger terminal 40 to receive the vehicle use service. Alternatively, the passenger terminal 40 may be a terminal positioned inside the vehicle, and the application 41 may be installed in the passenger terminal 40. For example, the passenger terminal 40 may be implemented in the form of the IVI positioned in two or more rows of the vehicle. Hereinafter, the transmission and reception of the signal by the control server 10 to and from the passenger terminal 40 through the application 41 may be represented by transmitting and receiving a signal to and from the passenger terminal 40.

Figure 2:
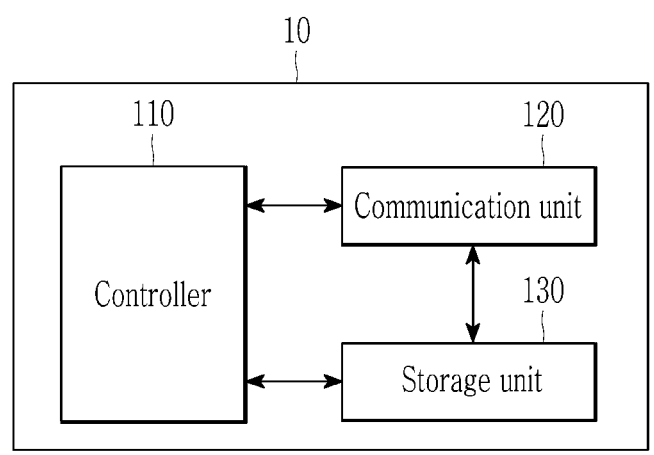
FIG. 2 is a block diagram schematically showing a configuration of a control server of FIG. 1.

FIG. 2 is a block diagram schematically showing a configuration of a control server of FIG. 1.

The control server 10 may include a controller 110, a communication unit 120, and a storage unit 130.

The controller 110 may determine the vehicle internal state from the air quality data received from the sensor unit 20 as one of the smoking state, the air pollution state, and the normal state, and may determine the driver evaluation score based on the evaluation score (hereinafter, the driving grade) for the driving received from the passenger terminal 40 according to the determined vehicle internal state, or the adjusted score to which a penalty is applied according to the determined vehicle internal state as the driver evaluation score for the driving. When the control server 10 receives a call request for the vehicle from the passenger terminal, based on the driver evaluation score for the driver, the control server 10 may transmit the call request to a specific driver terminal among a plurality of driver terminals or perform vehicle matching for the call request. For example, in transmitting the call request received from the passenger terminal to one of a plurality of driver terminals, the control server 10 may determine a priority of transmitting the call request based on the driver evaluation score.

The communication unit 120 may be connected to the sensor unit 20, the driver terminal 30, and the passenger terminal 40 through a wireless network to receive information necessary to provide the vehicle use service according to the control of the controller 110 or to transmit the control instructions. The communication unit 120 may receive the air quality data from the sensor unit 20 through a wired/wireless network. The communication unit 120 may transmit a signal indicating a smoking notification or a signal indicating an air pollution notification to the driver terminal 30 and the passenger terminal 40 based on the vehicle internal state determined by the controller 110 and request input of the driving grade to the passenger terminal 40 after ending the driving for the vehicle. The communication unit 120 may receive a signal indicating the driving grade from the passenger terminal 40.

The storage unit 130 may store the driver evaluation score in a database. The controller 110 may determine the driver evaluation score and update the determined driver evaluation score in the database.

Figure 3:
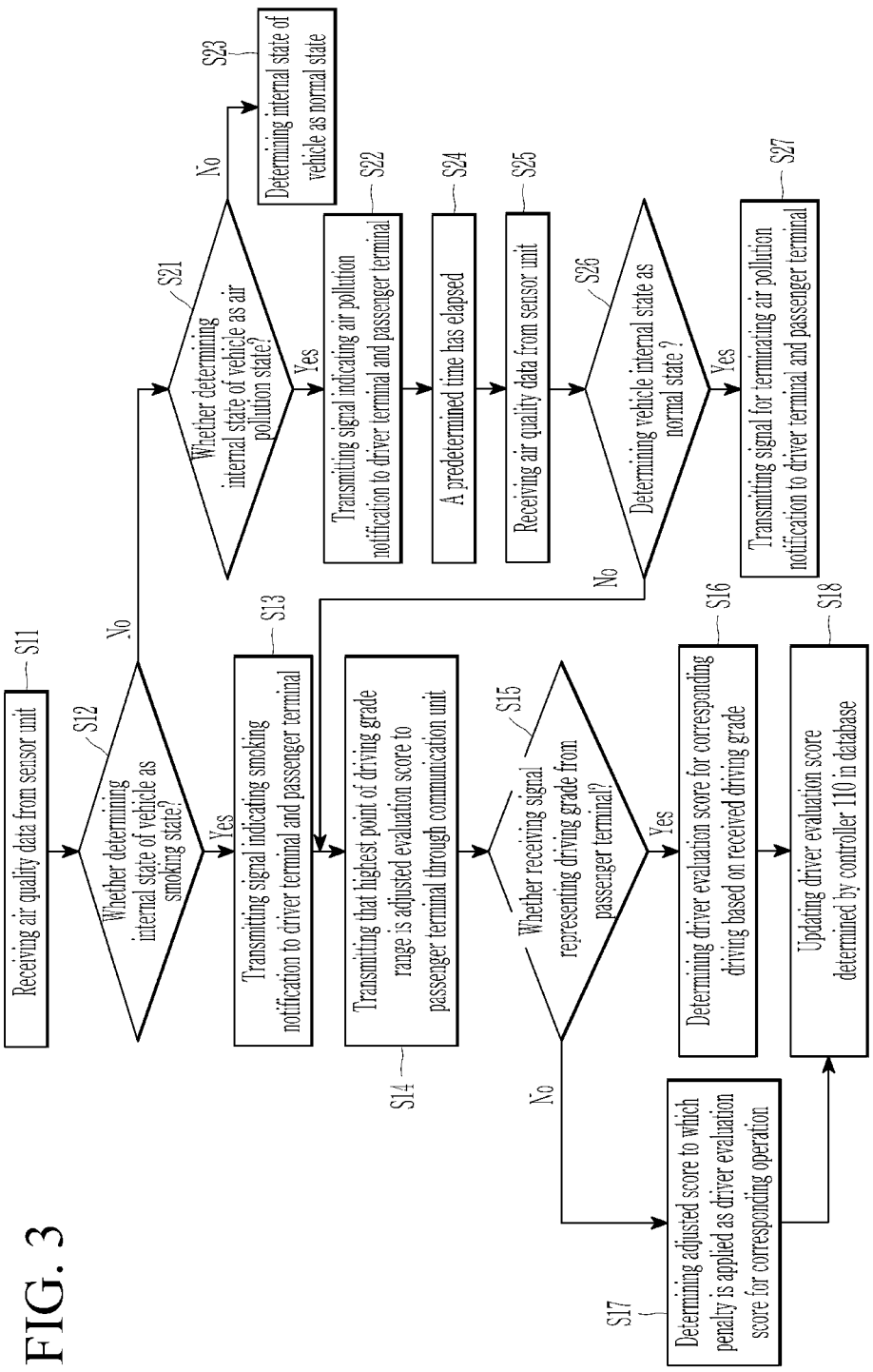
FIG. 3 is a flowchart of a driver evaluation management method according to an exemplary embodiment.

FIG. 3 is a flowchart of a driver evaluation management method according to an exemplary embodiment.

Hereinafter, with reference to FIG. 3, a method for determining the vehicle internal state as one among the smoking state, the air pollution state, and the normal state from the air quality data received from the sensor unit 20, providing the notification to the driver terminal 30 and the passenger terminal 40 according to the determined vehicle internal state, and determining the driver evaluation score based on the vehicle internal state will be described.

Based on a specific time point, the communication unit 120 may receive the air quality data from the sensor unit 20 (S11). Here, the specific time point may be any time point in the period from the start of the vehicle's operation to the end of the vehicle's operation.

The controller 110 may determine whether to determine the vehicle internal state as the smoking state based on the received air quality data (S12). The controller 110 may determine the vehicle internal state as the smoking state when the smoking value indicated by the air quality data is greater than or equal to a threshold smoking value. The threshold smoking value may be preset as initial information.

For example, the controller 110 may estimate an eCO2 value based on a TVOC value indicated by the air quality data and may determine the vehicle internal state as the smoking state based on the estimated eCO2 value.

In the step (S12), if the controller 110 determines the vehicle internal state as the smoking state, the communication unit 120 may transmit a signal indicating the smoking notification to the driver terminal 30 and the passenger terminal 40 (S13). The smoking notification may include content informing that the vehicle internal state is the smoking state.

The driver terminal 30 that has received the signal indicating the smoking notification from the communication unit 120 may inform the driver that the vehicle internal state is the smoking state. The passenger terminal 40 that has received the signal indicating the smoking notification from the communication unit 120 may inform the passenger that the vehicle internal state is the smoking state. For example, the driver terminal 30 or the passenger terminal 40 may indicate that it is the smoking state through a vibration or a sound, or it may display that it is the smoking state through a pop-up notification on the screen of the driver terminal 30 or the passenger terminal 40.

The controller 110 may request to check the usage fee and proceed with the payment of the usage fee to the passenger terminal 40 through the communication unit 120 after the operation of the vehicle is finished. The controller 110 may request to input the driving grade to the passenger terminal 40 after the operation of the vehicle is finished through the communication unit 120. At this time, the controller 110 may transmit that the highest point of the range (hereinafter, a driving grade range) of the evaluation score for the driving is the adjusted evaluation score to the passenger terminal 40 through the communication unit 120 (S14). The adjusted evaluation score is a score reduced by at least one step from the reference evaluation score, and the reference evaluation score may mean the highest score that may be evaluated for the driving by the passenger when the vehicle internal state is the normal state. The controller 110 may determine the adjusted evaluation score based on the reference evaluation score. For example, the controller 110 may determine the adjusted evaluation score of 4 stars based on the reference evaluation score of 5 stars. Or, for example, the controller 110 may determine the adjusted evaluation score of 90 points based on a reference evaluation score of 100 points.

The passenger terminal 40 that has received the input request of the driving grade from the communication unit 120 may display the driving grade range in which the adjusted score is the highest point on the screen, and display an input window in which the passenger may input the driving grade together. The passenger terminal 40 may receive the driving grade from the passenger and transmit the signal indicating the driving grade to the control server 10.

The controller 110 may handle the driver evaluation score differently depending on whether the signal representing the driving grade has been received from the passenger terminal through the communication unit 120.

When the communication unit 120 receives the signal representing the driving grade from the passenger terminal 40 (Yes at S15), the controller 110 may determine the driver evaluation score for the corresponding driving based on the received driving grade (S16). For example, the controller 110 may determine the received driving grade as the driver evaluation score for the corresponding driving. The fact that the communication unit 120 receives the signal indicating the driving grade from the passenger terminal 40 may indicate that the passenger inputs the driving grade based on the adjusted score to the passenger terminal 40.

If the communication unit 120 does not receive the signal indicating the driving grade from the passenger terminal (No at S15), the controller 110 may determine the adjusted score to which the penalty is applied for the corresponding operation as the driver evaluation score for the corresponding operation (S17). The fact that the communication unit 120 does not receive the signal indicating the driving grade from the passenger terminal 40 may indicate that the passenger does not input the driving grade based on the adjusted score to the passenger terminal 40. The adjusted score is a score that has decreased by at least one level from the reference score, the reference score may be the value given to the driver's operation when the vehicle internal state is the normal state, and the signal indicating the driving grade is not received from the passenger terminal. If the passenger does not input the driving grade to the passenger terminal 40, the penalty is applied to adjust the driver evaluation score directly from the control server 10.

For example, if the signal indicating the driving grade is not received from the passenger terminal 40, the controller 110 may determine the adjusted score of 4 stars as the driver evaluation score for the corresponding driving by applying the penalty of 1 star from 5 stars, which is the reference score. Alternatively, for example, if the signal indicating the driving grade is not received from the passenger terminal 40, the controller 110 may determine the adjusted score of 70 as the driver evaluation score for the corresponding driving by applying the penalty of 10 points to the reference score of 80 points.

Following the step (S16), or following the step (S17), the storage unit 130 may update the driver evaluation score determined by the controller 110 in the database (S18).

If the controller 110 does not determine the vehicle internal state as the smoking state (No at S12), the control server 10 may determine whether to determine the vehicle internal state as the air pollution state based on the received air quality data (S21). The controller 110 may determine the vehicle internal state as an air pollution state when the pollution level indicated by the air quality data is greater than or equal to the threshold pollution level. The threshold contamination level may be preset as initial information.

For example, the controller 110 may determine the vehicle internal state as the smoking state when the PM 2.5 value indicated by the air quality data is greater than or equal to the first threshold pollution level, or the PM 10 value indicated by the air quality data is greater than or equal to the second threshold pollution level.

When the controller 110 determines the vehicle internal state as the air pollution state (Yes as S21), the communication unit 120 may transmit the signal indicating the air pollution notification to the driver terminal 30 and the passenger terminal 40 (S22). The air pollution notification may include content informing that the vehicle internal state is the air pollution state, and may include content requesting ventilation of the vehicle.

If the controller 110 does not determine the vehicle internal state as the air pollution state (No at S21), the vehicle internal state may be determined as the normal state (S23).

Based on a specific time point at which a predetermined time has elapsed (S24) following the step (S22), the communication unit 120 may receive the air quality data from the sensor unit 20 (S25). Here, the predetermined time may be preset as initial information. For example, the control server 10 may receive the air quality data from the sensor unit 20 based on a time point after 10 minutes have elapsed from a time point when the signal indicating the air pollution notification is transmitted to the driver terminal 30 and the passenger terminal 40.

The controller 110 may determine whether to determine the vehicle internal state as the normal state based on the air quality data received (S26). When the pollution value indicated by the air quality data received in the step (S11) is less than the threshold pollution value, the controller 110 may determine the vehicle internal state as the normal state. Alternatively, the controller 110 may determine the vehicle internal state as the normal state based on the pollution value indicated by the air quality data received in the step (S11), if the pollution value indicated by the first air quality data received in the step (S25) has decreased within a predetermined range.

When the controller 110 determines the vehicle internal state as the normal state (Yes at S26), the communication unit 120 may transmit a signal for terminating the air pollution notification to the driver terminal 30 and the passenger terminal 40 (S27). For example, the communication unit 120 may transmit a signal to extinguish the pop-up notification displayed on the screen of the driver terminal 30 and the passenger terminal 40 in the step (S22) to the driver terminal 30 and the passenger terminal 40.

If the controller 110 does not determine the vehicle internal state as the normal state (No at S26), the step (S14) may proceed.

While this invention has been described in connection with what is presently considered to be practical exemplary embodiments, it is to be understood that the invention is not limited to the disclosed embodiments. On the contrary, it is intended to cover various modifications and equivalent arrangements included within the spirit and scope of the appended claims.

What is claimed is:

1. A driver evaluation method performed by a control server, the method comprising:
   receiving air quality data from a sensor in a vehicle at a specific time point which is any time point in a period from a start of operation of the vehicle to an end of the operation of the vehicle;
   determining an internal state of the vehicle as a smoking state, an air pollution state, or a normal state based on the air quality data;
   transmitting, in response to the determined internal state being the smoking state, a driving grade range to a passenger terminal, the driving grade range having an adjusted evaluation score reduced by at least one level from a reference evaluation score, which is a highest score when the determined internal state is the normal state, as a highest point;
   determining a driver evaluation score for driving of the vehicle based on a driving grade in response to the driving grade within the driving grade range being received from the passenger terminal;
   storing the driver evaluation score in a database;
   forwarding a call request to one of a plurality of driver terminals based on the driver evaluation score;
   transmitting a signal indicating air pollution to a driver terminal and the passenger terminal in response to the determined internal state being the air pollution state;
   receiving first air quality data from the sensor after a predetermined time has elapsed from transmission of the signal indicating the air pollution;
   determining whether the internal state is the normal state based on the first air quality data;
   transmitting a signal terminating the signal indicating the air pollution to the driver terminal and the passenger terminal in response to the internal state being determined as the normal state based on the first air quality data;
   determining the internal state of the vehicle as the smoking state when a smoking value indicated by the air quality data from the sensor is greater than or equal to a threshold smoking value;
   determining the internal state of the vehicle as the air pollution state when the internal state of the vehicle is not determined as the smoking state and a pollution level indicated by the air quality data is greater than or equal to a threshold pollution level; and
   determining the internal state of the vehicle as the normal state when the internal state of the vehicle is not determined as the air pollution state.

2. The method of claim 1, further comprising determining an adjusted score to which a penalty is applied as the driver evaluation score for the driving of the vehicle in response to the driving grade not being received from the passenger terminal.

3. The method of claim 1, further comprising determining the driver evaluation score for the driving of the vehicle based on the driving grade in response to the internal state not being determined as the normal state based on the first air quality data and the driving grade being received from the passenger terminal.

4. The method of claim 1, further comprising determining an adjusted score to which a penalty is applied as the driver evaluation score for the driving of the vehicle in response to the internal state not being determined as the normal state based on the first air quality data and the driving grade not being received from the passenger terminal.

5. The method of claim 1, further comprising determining the internal state as the normal state in response to the determined internal state not being the smoking state or the air pollution state.

6. A driver evaluation management system comprising:
   a sensor for inclusion in a vehicle and configured to measure a concentration of a smoking index capable of being determined as a smoking state and a pollution index capable of being determined as an air pollution state to generate air quality data; and
   a control server configured to:
   determine an internal state of the vehicle as the smoking state, the air pollution state, or a normal state based on the air quality data in response to the air quality data being received from the sensor at a specific time point which is any time point in a period from a start of operation of the vehicle to an end of the operation of the vehicle;
   provide a notification to a driver terminal and a passenger terminal in response to the internal state being determined as the smoking state or the air pollution state; and
   determine a driver evaluation score based on the internal state,
   wherein the control server comprises:
   a communication unit connected to the sensor, the driver terminal, and the passenger terminal via a network, the communication unit configured to:
   receive the air quality data from the sensor; and
   transmit the signal indicating a smoking notification or a signal indicating an air pollution notification to the driver terminal and the passenger terminal in response to the internal state being determined as the smoking state or the air pollution state, respectively;
   a controller configured to:
   determine the internal state as the smoking state, the air pollution state, or the normal state based on the air quality data; and determine the driver evaluation score based on a driving grade received from the passenger terminal according to the internal state or determine an adjusted evaluation score to which a penalty is applied as the driver evaluation score according to the determined internal state; and a storage unit configured to store the driver evaluation score in a database, wherein, in response to a determination that the internal state is the smoking state, the communication unit is configured to request input of the driving grade to the passenger terminal after driving of the vehicle is finished and transmit the adjusted evaluation score of which a highest point of a driving grade range is reduced by at least one level from a reference evaluation score which is a highest score when the determined internal state is the normal state, and wherein the control server is configured to forward a call request to one of a plurality of driver terminals based on the determined driver evaluation score, and, wherein, in response to a determination that the internal state is the air pollution state, the communication unit is configured to:

transmit a signal indicating the air pollution notification to the driver terminal and the passenger terminal;

receive first air quality data from the sensor after a certain time has elapsed from a time point at which the signal indicating the air pollution notification was transmitted;

determine whether the internal state is the normal state based on the first air quality data; and transmit a signal terminating the signal indicating the air pollution state to the driver terminal and the passenger terminal in response to the internal state being determined as the normal state based on the first air quality data, wherein the controller is configured to:

determine the internal state of the vehicle as the smoking state when a smoking value indicated by the air quality data is greater than or equal to a threshold smoking value;

determine the internal state of the vehicle as the air pollution state when the internal state of the vehicle is not determined as the smoking state and a pollution level indicated by the air quality data is greater than or equal to a threshold pollution level; and determine the internal state of the vehicle as the normal state when the internal state of the vehicle is not determined as the air pollution state.

7. The driver evaluation management system of claim 6, wherein in response to a signal indicating the driving grade is received from the passenger terminal, the controller is configured to determine the driver evaluation score based on the received driving grade.

8. The driver evaluation management system of claim 6, wherein in response to a signal indicating the driving grade not being received from the passenger terminal, the controller is configured to determine the adjusted evaluation score to which the penalty is applied as the driver evaluation score.

9. The driver evaluation management system of claim 6, wherein the controller is configured to determine whether the internal state is the normal state based on the first air quality data.

10. The driver evaluation management system of claim 9, wherein in response to a determination that the internal state is not the normal state, the communication unit is configured to:

request input of the driving grade to the passenger terminal after driving of the vehicle is finished; and transmit the adjusted evaluation score of which the highest point of the driving grade range is reduced by at least one level from the reference evaluation score.

11. The driver evaluation management system of claim 10, wherein, in response to a signal indicating the driving grade not being received from the passenger terminal, the controller is configured to determine the adjusted evaluation score to which the penalty is applied as the driver evaluation score.

* * * * *

UNITED STATES PATENT AND TRADEMARK OFFICE
CERTIFICATE OF CORRECTION

| | | |
|---|---|---|
| PATENT NO. | : 12,198,089 B2 | Page 1 of 1 |
| APPLICATION NO. | : 17/734565 | |
| DATED | : January 14, 2025 | |
| INVENTOR(S) | : Hanul Lee and Sojeong Kim | |

It is certified that error appears in the above-identified patent and that said Letters Patent is hereby corrected as shown below:

In the Claims

In Column 10, Line 58, Claim 6:
Change "transmit the signal indicating a smoking notification"
To --transmit a signal indicating a smoking notification--

In Column 11, Line 23, Claim 6:
Change "transmit a signal indicating the air pollution notification"
To --transmit the signal indicating the air pollution notification--

Signed and Sealed this
Fourth Day of March, 2025

Coke Morgan Stewart
*Acting Director of the United States Patent and Trademark Office*